US012580071B2

(12) United States Patent
Kunz et al.

(10) Patent No.: US 12,580,071 B2
(45) Date of Patent: Mar. 17, 2026

(54) SYSTEMS AND METHODS TO PROCESS ELECTRONIC IMAGES WITH AUTOMATIC PROTOCOL REVISIONS

(71) Applicant: PAIGE.AI, Inc., New York, NY (US)

(72) Inventors: Jeremy Daniel Kunz, New York, NY (US); Donghun Lee, New York, NY (US)

(73) Assignee: Paige.AI, Inc., New York, NY (US)

( * ) Notice: Subject to any disclaimer, the term of this patent is extended or adjusted under 35 U.S.C. 154(b) by 494 days.

(21) Appl. No.: 18/316,711

(22) Filed: May 12, 2023

(65) Prior Publication Data

US 2023/0368899 A1     Nov. 16, 2023

Related U.S. Application Data

(60) Provisional application No. 63/341,504, filed on May 13, 2022.

(51) Int. Cl.
    *G16H 30/40*       (2018.01)
    *G06V 10/70*       (2022.01)
            (Continued)

(52) U.S. Cl.
    CPC ............. *G16H 30/40* (2018.01); *G06V 10/70* (2022.01); *G16H 15/00* (2018.01); *G16H 30/20* (2018.01)

(58) Field of Classification Search
    CPC ........ G16H 30/40; G16H 15/00; G16H 30/20; G16H 50/20; G16H 50/70; G16H 70/20;
        (Continued)

(56) References Cited

U.S. PATENT DOCUMENTS

2020/0161005 A1*   5/2020   Lyman ................... G16H 50/20

FOREIGN PATENT DOCUMENTS

| CN | 112614573 A | 4/2021 | |
| WO | 2020185660 A1 | 9/2020 | |
| WO | WO-2021044431 A1 * | 3/2021 | ............. G16H 50/20 |

OTHER PUBLICATIONS

Harrison Jr., James H., et al. "Introduction to artificial intelligence and machine learning for pathology." Archives of pathology & laboratory medicine 145.10 (Oct. 2021): 1228-1254.

* cited by examiner

*Primary Examiner* — Neil R Mclean

(74) *Attorney, Agent, or Firm* — Bookoff McAndrews, PLLC

(57)         ABSTRACT

Systems and methods are described herein for processing electronic medical images. The method may include determining, using an automated routine, whether a pathology protocol is accessible; determining a first set of one or more training images, the first set of one or more training images comprising digital medical images annotated utilizing the pathology protocol; and providing the training images to a machine learning model capable of analyzing digital medical images according to the pathology protocol or guideline. The providing may further include determining a starting model, splitting the first set of one or more training images into a training set A and an evaluation set B of digital medical images, fine tuning the starting model with the training set A to determine the machine learning model, evaluating the machine learning model with the training set B, and upon receiving a passing evaluation, saving the determined machine learning model.

20 Claims, 7 Drawing Sheets

(51) Int. Cl.
   *G16H 15/00*          (2018.01)
   *G16H 30/20*          (2018.01)
(58) Field of Classification Search
   CPC .... G16H 70/60; G06V 10/70; G06V 10/7747;
               G06V 10/776; G06V 2201/03; G06N
                            20/00
   USPC ........................................................ 382/128
   See application file for complete search history.

<u>200</u>　　CAP　　　　　　　　　　　　　　　　　　　BREAST.DCIS_4.4.0.0.REL_CAPCP
　　　　APPROVED
　　　　　REPORTING TEMPLATE
_____

PROTOCOL POSTING DATE: JUNE 2021
SELECT SINGLE RESPONSE UNLESS OTHERWISE INDICATED.

CASE SUMMARY: (DCIS OF THE BREAST: RESECTION)
STANDARD(S): AJCC-UICC 8

SPECIMEN

PROCEDURE(NOTE <u>A</u>)
__ EXCISION (LESS THAN TOTAL MASTECTOMY)
__ TOTAL MASTECTOMY (INCLUDING NIPPLE-SPARING AND SKIN-SPARING MASTECTOMY)
__ OTHER (SPECIFY): _____
__ NOT SPECIFIED

SPECIMEN LATERALITY
__ RIGHT
__ LEFT
__ NOT SPECIFIED

TUMOR

+TUMOR SITE(NOTE <u>B</u>) (SELECT ALL THAT APPLY)
__ UPPER OUTER QUADRANT
__ LOWER OUTER QUADRANT
__ UPPER INNER QUADRANT
__ LOWER INNER QUADRANT
__ CENTRAL
__ NIPPLE
__ CLOCK POSITION
　　SPECIFY CLOCK POSITION (SELECT ALL THAT APPLY)
　　__ 1 O'CLOCK
　　__ 2 O'CLOCK
　　__ 3 O'CLOCK
　　__ 4 O'CLOCK
　　__ 5 O'CLOCK
　　__ 6 O'CLOCK
　　__ 7 O'CLOCK
　　__ 8 O'CLOCK
　　__ 9 O'CLOCK
　　__ 10 O'CLOCK
　　__ 11 O'CLOCK
　　__ 12 O'CLOCK

__ SPECIFY DISTANCE FROM NIPPLE IN CENTIMETERS (CM): _____ CM
__ OTHER (SPECIFY): _____
__ NOT SPECIFIED

FIG. 2

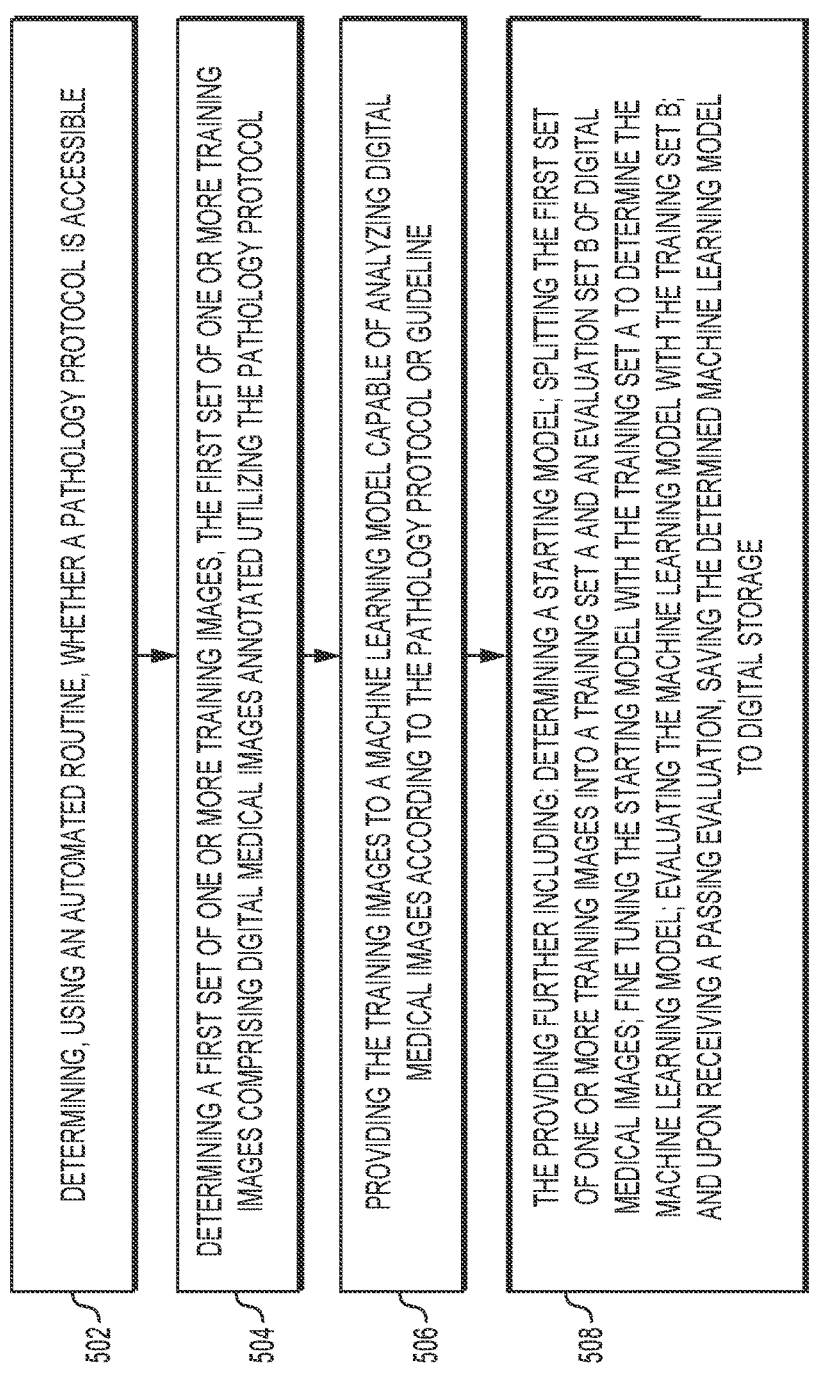

500

502 DETERMINING, USING AN AUTOMATED ROUTINE, WHETHER A PATHOLOGY PROTOCOL IS ACCESSIBLE

504 DETERMINING A FIRST SET OF ONE OR MORE TRAINING IMAGES, THE FIRST SET OF ONE OR MORE TRAINING IMAGES COMPRISING DIGITAL MEDICAL IMAGES ANNOTATED UTILIZING THE PATHOLOGY PROTOCOL

506 PROVIDING THE TRAINING IMAGES TO A MACHINE LEARNING MODEL CAPABLE OF ANALYZING DIGITAL MEDICAL IMAGES ACCORDING TO THE PATHOLOGY PROTOCOL OR GUIDELINE

508 THE PROVIDING FURTHER INCLUDING: DETERMINING A STARTING MODEL; SPLITTING THE FIRST SET OF ONE OR MORE TRAINING IMAGES INTO A TRAINING SET A AND AN EVALUATION SET B OF DIGITAL MEDICAL IMAGES; FINE TUNING THE STARTING MODEL WITH THE TRAINING SET A TO DETERMINE THE MACHINE LEARNING MODEL; EVALUATING THE MACHINE LEARNING MODEL WITH THE TRAINING SET B; AND UPON RECEIVING A PASSING EVALUATION, SAVING THE DETERMINED MACHINE LEARNING MODEL TO DIGITAL STORAGE

FIG. 5

SYSTEMS AND METHODS TO PROCESS ELECTRONIC IMAGES WITH AUTOMATIC PROTOCOL REVISIONS

CROSS-REFERENCE TO RELATED APPLICATION(S)

This application claims the benefit of priority to U.S. Provisional Patent Application No. 63/341,504, filed May 13, 2022, the entirety of which is incorporated by reference herein. Further, U.S. Provisional Patent Application No. 63/341,825, filed May 13, 2022, is incorporated by reference in its entirety.

TECHNICAL FIELD

Various embodiments of the present disclosure pertain generally to image processing. More specifically, particular embodiments of the present disclosure relate to systems and methods to automatically update protocols for processing electronic images.

BACKGROUND

Within the field of pathology, hospitals and institutions such as the College of American Pathologists ("CAP") establish guidelines, existing protocols, synoptic reports, and worksheets (collectively referred to as "guidelines" or "protocols") for pathologist and researchers to adhere to during analysis. The guidelines may provide standard practices and reporting techniques for pathologist/researchers. These guidelines may be updated frequently, and pathologist and hospital workers may need to stay up to date with the best practices based on the guidelines.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY OF THE DISCLOSURE

According to certain aspects of the present disclosure, systems and methods are disclosed for processing electronic medical images. In one aspect, a computer-implemented method for processing electronic medical images to determine, using an automated routine, whether a pathology protocol is accessible; determining a first set of one or more training images, the first set of one or more training images comprising digital medical images annotated utilizing the pathology protocol; and providing the training images to a machine learning model capable of analyzing digital medical images according to the pathology protocol or guideline. The providing may further include determining a starting model; splitting the first set of one or more training images into a training set A and an evaluation set B of digital medical images; fine tuning the starting model with the training set A to determine the machine learning model; evaluating the machine learning model with the training set B; and upon receiving a passing evaluation, saving the determined machine learning model to digital storage.

The method may further include, upon determining that a pathology protocol is available further comprises: parsing data of the pathology protocol; determining a new synoptic report based on the parsed data; and providing the new synoptic report to the machine learning model.

The training images may include annotations of digital medical images, the annotations being performed according to the pathology protocol, wherein the annotations comprise measurements, designations, and/or diagnoses.

Determining whether a pathology protocol is available may be performed iteratively at predetermined time intervals. The pathology protocol may be a new cancer protocol template. The pathology protocol may be a PDF, word document, or CSV document. The starting model in a machine learning model may be trained on a previous version of the pathology protocol.

The method may further include determining a new synoptic report based on the pathology guideline, the machine learning model being trained to fill out the new synoptic report when analyzing new digital medical images.

Determining a new synoptic report may include automatically creating, by a machine learning system and/or a rules-based artificial intelligence algorithm, a new synoptic report. Demining a new synoptic reports may include receiving a synoptic report corresponding to the pathology protocol or guideline from an external user or system. The machine learning model may not be determined until the determined first set of one or more training images exceed a threshold value of training images.

The method may further include determining the machine learning model has been applied to a predetermined number of slides to meet a study requirement.

According to certain aspects of the present disclosure, systems and methods are disclosed for processing electronic medical images. In another aspect, a system for processing electronic digital medical images may comprise at least one memory storing instructions and at least one processor configured to execute the instructions to perform operations. The at least one processor may comprise determining, using an automated routine, whether a pathology protocol is accessible; determining a first set of one or more training images, the first set of one or more training images comprising digital medical images annotated utilizing the pathology protocol; and providing the training images to a machine learning model capable of analyzing digital medical images according to the pathology protocol or guideline. The providing may further include determining a starting model; splitting the first set of one or more training images into a training set A and an evaluation set B of digital medical images; fine tuning the starting model with the training set A to determine the machine learning model; evaluating the machine learning model with the training set B; and upon receiving a passing evaluation, saving the determined machine learning model to digital storage.

According to certain aspects of the present disclosure, systems and methods are disclosed for processing electronic medical images. In another aspect, a non-transitory computer-readable medium storing instructions that, when executed by a processor, perform operations processing electronic digital medical images, is disclosed. The operations may include determining, using an automated routine, whether a pathology protocol is accessible; determining a first set of one or more training images, the first set of one or more training images comprising digital medical images annotated utilizing the pathology protocol; and providing the training images to a machine learning model capable of analyzing digital medical images according to the pathology protocol or guideline. The providing may further include determining a starting model; splitting the first set of one or more training images into a training set A and an evaluation set B of digital medical images; fine tuning the starting model with the training set A to determine the machine learning model; evaluating the machine learning model with the training set B; and upon receiving a passing evaluation, saving the determined machine learning model to digital storage.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims. As will be apparent from the embodiments below, an advantage to the disclosed systems and methods is that multiple parties may fully utilize their data without allowing others to have direct access to raw data. The disclosed systems and methods discussed below may allow advertisers to understand users' online behaviors through the indirect use of raw data and may maintain privacy of the users and the data.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 2 depicts an exemplary section of a College of American Pathologist ("CAP") protocol.

FIG. 5 is a flowchart illustrating an example method for determining an AI model to analyze digital medical images utilizing a new version of a guideline/protocol.

DETAILED DESCRIPTION OF EMBODIMENTS

Figure 1A:
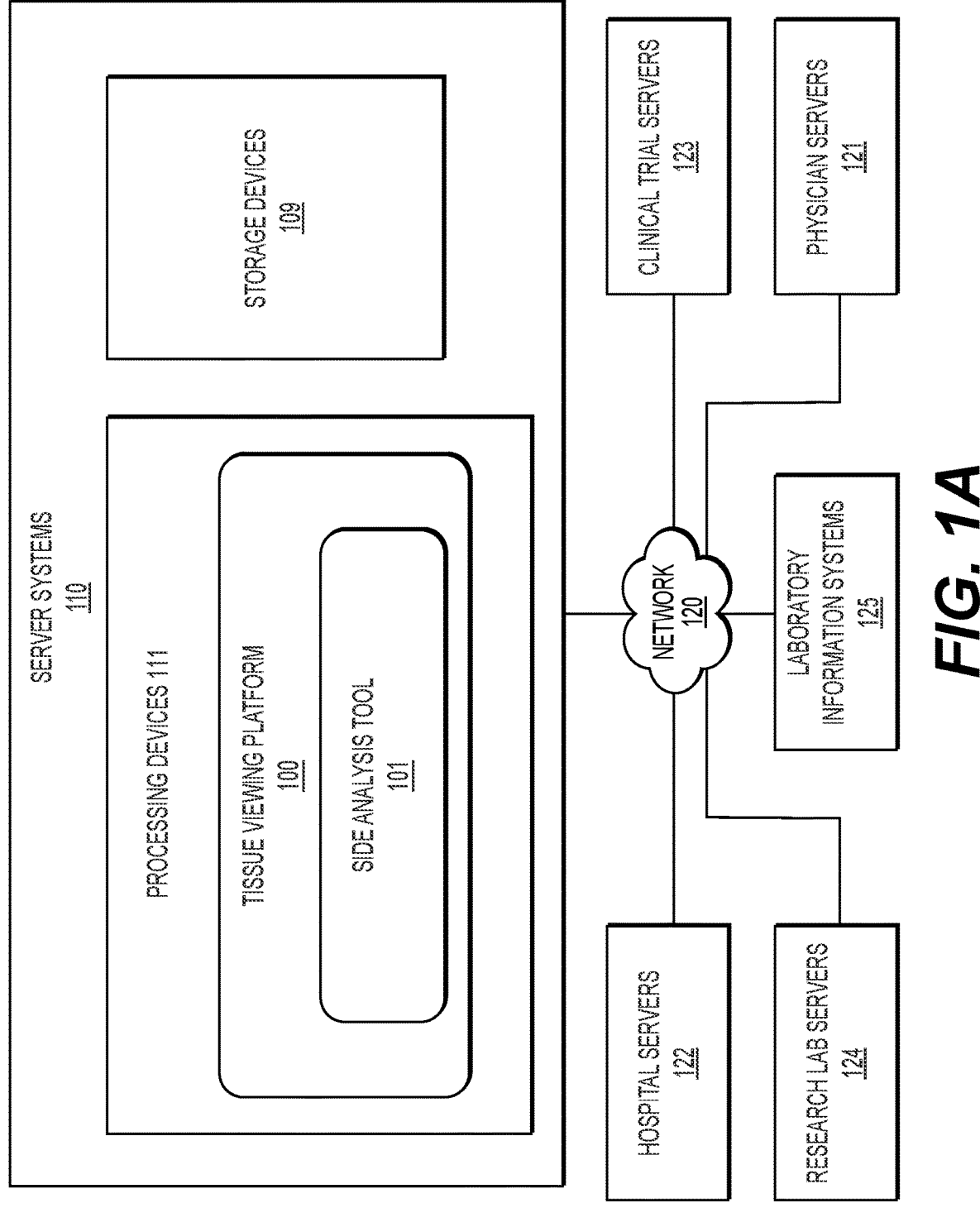
FIG. 1A illustrates a block diagram of a system and network for processing images to determine one or more machine learning models trained on a new protocol or guideline, according to an exemplary technique of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

As used herein, a "machine learning model" generally encompasses instructions, data, and/or a model configured to receive input, and apply one or more of a weight, bias, classification, or analysis on the input to generate an output. The output may include, for example, a classification of the input, an analysis based on the input, a design, process, prediction, or recommendation associated with the input, or any other suitable type of output. A machine learning model is generally trained using training data, e.g., experiential data and/or samples of input data, which are fed into the model in order to establish, tune, or modify one or more aspects of the model, e.g., the weights, biases, criteria for forming classifications or clusters, or the like. Deep learning techniques may also be employed. Aspects of a machine learning model may operate on an input linearly, in parallel, via a network (e.g., a neural network), or via any suitable configuration.

The execution of the machine learning model may include deployment of one or more machine learning techniques, such as linear regression, logistical regression, random forest, gradient boosted machine (GBM), deep learning, and/or a deep neural network. Supervised and/or unsupervised training may be employed. For example, supervised learning may include providing training data and labels corresponding to the training data, e.g., as ground truth. Unsupervised approaches may include clustering, classification or the like. K-means clustering or K-Nearest Neighbors may also be used, which may be supervised or unsupervised. Combinations of K-Nearest Neighbors and an unsupervised cluster technique may also be used. Any suitable type of training may be used, e.g., stochastic, gradient boosted, random seeded, recursive, epoch or batch-based, etc.

Techniques described herein may be utilized by hospital/ research centers to stay up to date with the latest CAP and other pathology and/or cancer protocol and/or guideline templates. Adapting protocol changes for worksheet/synoptic reports may be time consuming. Protocol changes may include events such as the renaming of fields within a protocol, removal of a field within a protocol, the addition of a field in a protocol. An exemplary protocol change may include: A protocol change may also involve the combination of one or more fields within a protocol template. An example protocol update may rename a field of a worksheet. The previous version of the worksheet may have had a field named "invades bladder neck," and the updated protocol may rename the field "invades bladder neck tissue." An exemplary protocol change may include, e.g CAP Breast DCIS Protocol Summary of Changes v4.2.0.0, the modified elements being for the margins: options added for reporting distance from closest uninvolved margin; distances added from other uninvolved margins; responses modified for positive margins; and ENE may now be a core element. Another exemplary protocol change may include, e.g., for the CAP Breast DCIS Protocol Summary of Changes v4.3.0.1 where margins are updated in the footnote for focality of involved margins; and the following data elements may be modified: the closest uninvolved DCIS margin(s) may be specified and may now conditionally be required if <2 mm; and non-core reporting section may be added to report distance to other margins if margins are involved. Another exemplary protocol change may include, general reformatting, revised margins section, revised lymph node section, added distant metastasis section, and removed pNX staging classification.

Automatically creating digital worksheets/synoptic reports to reflect updated protocol may simplify the workflow of pathologists. It may be advantageous to have a system trained to analyze a protocol template, determine that a field name is an older version such as "invades bladder neck" and update the field name to a newer version such as "invades bladder neck tissue." The system may automate the process of creating synoptic reports/worksheets that are up to date with the latest, or any predetermined, CAP guidelines/protocol and/or hospital-specific protocol. The system may further create/update a machine learning or artificial intelligence ("AI") model capable of analyzing whole slide images ("WSI") based on the new protocol. This mitigates difficulties with manually fine tuning models based on new worksheets, which may be tedious and time consuming.

FIG. 1A illustrates a block diagram of a system and network for processing images to determine one or more machine learning models trained on a new protocol or guideline, according to an exemplary technique of the present disclosure.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an exemplary embodiment of the present disclosure, the electronic network 120 may also be connected to server systems 110, which may include processing devices 111. One or more of the processing devices 111 may be configured to determine a machine learning module, which may be performed by a slide analysis tool 101 and/or protocol tool 141 for determining one or more AI models based on a new protocol or guideline, according to an exemplary technique described herein.

The physician servers 121, hospital servers 122, clinical trial servers 123, research lab servers 124, and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server systems 110 may include one or more storage devices 109 for storing images and data received from at least one of the physician servers 121, hospital servers 122, clinical trial servers 123, research lab servers 124, and/or laboratory information systems 125. Server systems 110 may also include processing devices 111 for processing images and data stored in the one or more storage devices 109. Server systems 110 may further include one or more machine learning tool(s) or capabilities. For example, the processing devices 111 may include a machine learning tool for the machine learning module (e.g., protocol tool 141), according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides. In hospital settings, tissue type information may be stored in one of the laboratory information systems 125.

Figure 1B:
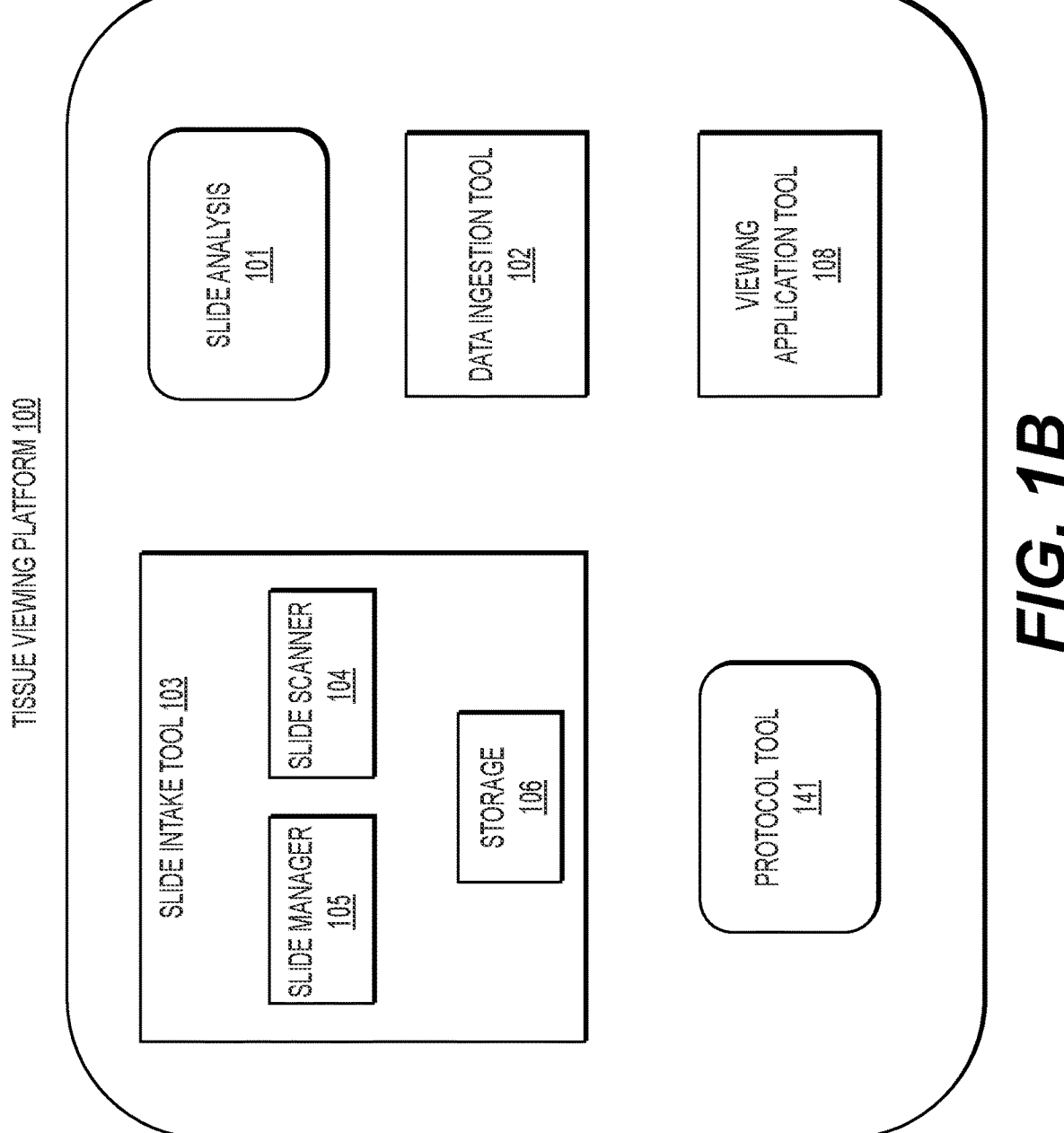
FIG. 1B illustrates an exemplary block diagram of a tissue viewing platform according to techniques presented herein.

FIG. 1B illustrates an exemplary block diagram of a tissue viewing platform 100 for determining one or more machine learning models to apply pertaining to digital pathology image(s), the determined machine learning models being capable of analyzing digital medical images according to a new protocol or guideline.

For example, the tissue viewing platform 100 may include the slide analysis tool 101, a data ingestion tool 102, a slide intake tool 103, a slide scanner 104, a slide manager 105, a storage 106, a viewing application tool 108, and a protocol tool 141.

The slide analysis tool 101, as described in detail below, refers to a process and system for processing digital pathology slides (e.g., digitized images of slide-mounted histology or cytology specimens) and received AI models, and using machine learning to analyze and determine one or more machine learning systems to output based on a search criteria, according to an exemplary embodiment. The slide analysis tool 101 may further apply the determined machine learning systems to one or more digital pathology slides.

The data ingestion tool 102 refers to a process and system for facilitating a transfer of the digital pathology images to the various tools, modules, components, and devices that may be used for classifying and processing the digital pathology images, according to an exemplary embodiment.

The slide intake tool 103 refers to a process and system for scanning pathology slides and converting them into a digital form, according to an exemplary embodiment. The slides may be scanned with the slide scanner 104, and the slide manager 105 may process the images on the slides into digitized pathology images and store the digitized images in storage 106.

The viewing application tool 108 refers to a process and system for providing a user (e.g., a pathologist) with specimen property or image property information pertaining to digital pathology image(s), according to an exemplary embodiment. The information may be provided through various output interfaces (e.g., a screen, a monitor, a storage device, and/or a web browser, etc.).

The slide analysis tool 101, and one or more of its components, may transmit and/or receive digitized slide images and/or patient information and/or AI models to server systems 110, physician servers 121, hospital servers 122, clinical trial servers 123, research lab servers 124, and/or laboratory information systems 125 over an electronic network 120. Further, server systems 110 may include one or more storage devices 109 for storing images, AI models, and data received from at least one of the slide analysis tool 101, the data ingestion tool 102, the slide intake tool 103, the slide scanner 104, the slide manager 105, the viewing application tool 108, and protocol tool 141. Server systems 110 may also include the processing devices 111 for processing images and data stored in the storage devices 109. Server systems 110 may further include one or more machine learning tool(s) or capabilities, e.g., due to the processing devices 111. Alternatively or in addition, the present disclosure (or portions of the system and methods of the present disclosure) may be performed on a local processing device (e.g., a laptop).

The protocol tool 141 as described in greater detail below, refers to a process and system for processing digital pathology slides (e.g., digitalized images of a slide-mounted history or cytology specimens), and using machine learning or a rules based system for determining analysis of a digital medical image according to a new and/or updated protocol or guideline.

Any of the above devices, tools and modules may be located on a device that may be connected to an electronic network 120, such as the Internet or a cloud service provider, through one or more computers, servers, and/or handheld mobile devices.

The systems and methods described herein may allow for pathologists to be notified when a new public or internal protocol is developed. For example, the system may determine that a new version of CAP guideline or protocol has been developed. This may allow pathologist to learn of new guidelines as soon as the protocol is developed. Further, the system may save pathologist/hospitals time by automatically creating worksheet versions based on the new guidelines.

The system may further determine a trained machine learning system (e.g., protocol tool 141) capable of analyzing digital medical images to perform a diagnosis and/or measurement while utilizing the newly determined protocol or guideline, as will be further described herein. The trained system may allow for model fine-tuning once a minimum number of slides are present sufficient to train the system. By automatically determining and/or updating AI models for new CAP guidelines and protocols/synoptic worksheets, a hospital may be able to develop AI models faster. This may further keep AI models updated based on the latest guidelines and/or protocols. Once these AI models are developed, in one technique the work of pathologist may be reviewed and compared with the AI models for accuracy.

Further, the system may help with preparation for a study by the Food and Drug Administration (FDA), Conformité Européenne (CE), or Food, Drug, & Cosmetic (FDRC) to approve the created AI model as described later herein.

FIG. 2 depicts an exemplary section of a College of American Pathologist protocols. In particular, FIG. 2 depicts a section of the Protocol for the Examination of Resection Specimen from Patients with ductal Carcinoma in Situ (DCIS) of the Breast version 4.4.0.0 released in June of 2021 ("Breast DCIS, Resection Protocol") 200. The systems and methods described herein may be capable of analyzing one or more digital medical images according to this exemplary protocol. Further, the systems and methods described herein may determine when this version of the Breast DCIS, Resection protocol was created and determine a synoptic report based on this protocol. For example, the system may determine that previous versions of the Breast DCIS, Resection protocol were released in February 2020 (version 4.3.0.2), September 2019 (version 4.3.0.1), August 2019

(version 4.3.0.0), and February 2019 (version 4.2.0.0). The systems and methods described herein may further be capable of determining updates to the protocol. For example, for the Breast DCIS, Resection Protocol for 4.4.0.0 updated general reformatting, revised margins section, revised lymph node section, added distant metastasis section, and removed pNX staging classification. The systems and method described herein may be capable of analyzing digital medical images according to CAP protocol related to Breast (e.g., Breast DCIS, Resection; Breast DCIS, Biopsy; Breast Phyllodes Tumor; Breast Invasive, Resection; Breast Invasive, Biopsy; or Breast Biomarker Reporting), Central Nervous System, Endoctrine (e.g., Adrenal Gland, Appendix NET, Colon NET, Duodenum and Ampulla NET, Jejunum and Ileum NET, Pancreas Endocrine, Stomach NET, Thyroid, or Thyroid Biomarker Reporting), Gastrointestinal (e.g., Ampulla of Vater; Anus, Excision; Anus, Resection; Appendix; Colon and Rectum, Biopsy; Colon and Rectum, Resection; Colon and Rectum Biomarker Reporting; Distal Extrahepatic Bile Ducts; Esophagus; Gallbladder; GIST, Biopsy; GIST, Resection; GIST Biomarker Reporting; Hepatocellular Carcinoma; Intrahepatic Bile Ducts; Pancreas (Exocrine); Perihilar Bile Ducts; Small Intestine; Stomach; or Gastric HER2 Biomarker Reporting), Genitourinary (e.g., Kidney, Biopsy; Kidney, Resection; Penis; Prostate Needle Biopsy Case Level; Prostate Needle Biopsy Specimen Level; Prostate, Resection; Prostate TURP; Testis Radical Orchiectomy; Testis Lymphadenectomy; Ureter, Renal Pelvis, Biopsy; Ureter, Renal Pelvis, Resection; Urethra, Biopsy; Urethra, Resection; Urinary Bladder, Resection; Urinary Bladder, or Biopsy), Gynecologic (e.g., Endometrium Uterus; Endometrium Biomarker Reporting *RETIRED*; Gynecologic, Biomarkers *NEW*; Ovary, Fallopian Tube, or Peritoneum; Trophoblastic Tumors; Uterine Cervix, Excision; Uterine Cervix, Resection; Uterine Sarcoma; Vagina, Biopsy; Vagina, Resection; or Vulva), Head and Neck (e.g., Larynx, Oral Cavity, Major Salivary Glands, Nasal Cavity and Paranasal Sinuses, Pharynx, Head and Neck Biomarker Reporting, or Head and Neck Biomarker Reporting), Hematologic (e.g., Bone Marrow, Hodgkin Lymphoma, Non-Hodgkin Lymphoma, or Plasma Cell Neoplasms), Ophthalmic (e.g., Retinoblastoma, or Uveal Melanoma), Pediatric (e.g., Ewing, Resection; Ewing, Biopsy; Germ Cell Tumor, Resection; Germ Cell Tumor, Biopsy; Hepatoblastoma, Resection; Hepatoblastoma, Biopsy; Neuroblastoma, Resection; Neuroblastoma, Biopsy; Rhabdomyosarcoma, Resection; Rhabdomyosarcoma, Biopsy; Wilms, Resection; or Wilms, Biopsy), Skin (e.g., Skin, Melanoma, Biopsy; Skin, Melanoma, Excision; Melanoma Biomarker Reporting; or Merkel Cell Carcinoma), Thorax (e.g., Lung, Resection; Lung Biomarker Reporting; Pleural Mesothelioma; or Thymus), Bone and Soft Tissue (e.g., Bone, Biopsy; Bone, Resection; Soft Tissue, Biopsy; or Soft Tissue, Resection), or General (e.g., DNA Mismatch Repair Biomarker Reporting; Generic Template, Biopsy; Generic Template, Resection; or General IHC Quantitative Biomarkers).

The systems and method described herein may be capable of analyzing digital medical images according to alternative pathology and/or cancer protocol templates (e.g., the Royal college of Pathologist of Australasia protocols, or the International Collaboration of Cancer Reporting protocols). For example, the systems and methods may be applied to hospital specific guideline and/or protocols.

Figure 3:
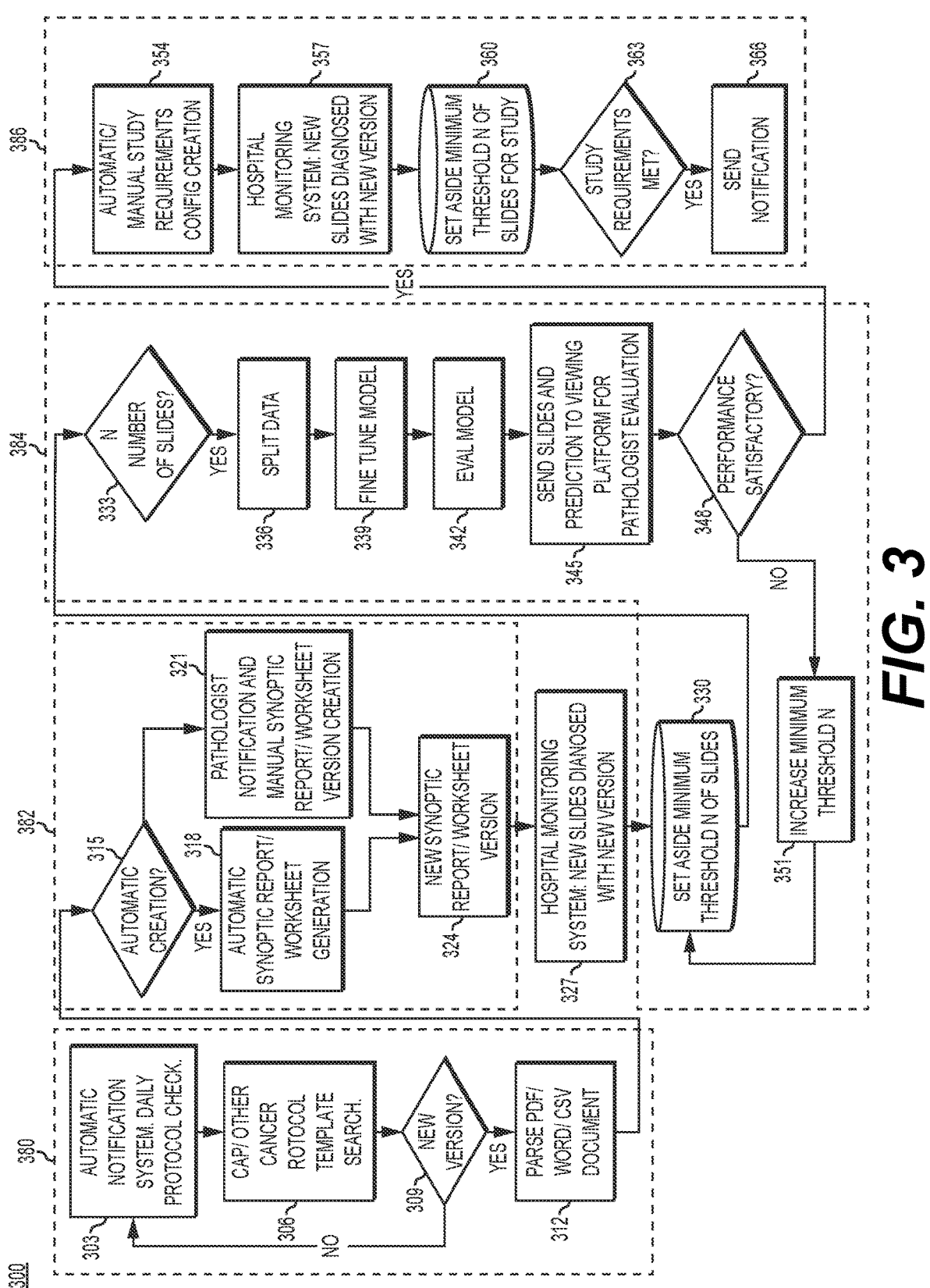
FIG. 3 depicts an exemplary block diagram of a system and network to determine an AI model to analyze digital medical images utilizing a new version of a guideline/protocol, according to an exemplary embodiment of the present disclosure.

FIG. 3 depicts an exemplary block diagram 300 of a system and network to determine a machine learning system to analyze digital medical images utilizing a new version of a guideline/protocol, according to an exemplary embodiment of the present disclosure. The trained system may be implemented by the protocol tool 141 of the tissue viewing platform 100.

FIG. 3's block diagram may include four larger steps: (1) function 380 for determining if new protocol exists, (2) function 382 for determining a new report/worksheet, (3) function 384 determining and/or updating a new machine learning system, and/or (4) step 386 for determining that study requirements have been met. In one example, these four functions may all be implemented by the protocol tool 141 and/or slide analysis tool 101 of the tissue viewing platform 100. In another example, individual functions of the block diagram 300 (e.g., determining a new report/worksheet) may be determined by a separate computer processing system capable of receiving image inputs such as device 600 and sent to the tissue viewing platform 100 by the network 120. In some examples, only certain steps may be utilized. For example, the system might only complete steps 380, 382, and 384, while step 386 might not be performed in an embodiment. In other embodiments, only a single of the steps 380, 382, 384, or 386 may occur.

At step 380, the trained system described herein may determine that a new public and/or internal protocol version has been created, as shown with steps 303, 306, and 309 of FIG. 3. Further, at step 380, upon determining a new protocol exists, the new protocol and/or guideline may be parsed at step 312. An exemplary protocol version is the Examination of Resection Specimen from Patients with ductal Carcinoma in Situ (DCIS) of the Breast version 4.4.0.0 released in June of 2021 from FIG. 2. In one example, of step 380, the trained system may search for a particular protocol or guideline. In another example, the trained system may search for updates to any of the protocol or guidelines for a hospital and/or CAP.

At step 303, the trained system may prepare to perform web scraping on the CAP website and/or internal hospital websites. This search may automatically occur iteratively at certain time periods such as once a day, once a week, once a month, etc. A user may be able to select how often the web scraping search is conducted. In one example, this search may be performed on an automated routine, such as once a day. This search, along with steps 306 and 309 may determine whether a new pathology protocol is accessible.

At step 306, the trained system may perform web scraping on any other website or system that stores protocols and/or guidelines. Web scraping may include both fetching and extracting the data, wherein the data may refer to a new guideline or protocol. Exemplary web scraping techniques may include, but are not limited to, human copy-and-paste, text pattern matching, HTTP programing, HTML parsing, DOM parsing, vertical aggregation, semantic annotation recognizing, and computer vision web-page analysis. For example, the web scraping may be performed on the Cancer Protocol Templates webpage of the College of American Pathologists (cap.org). Alternatively, a user may provide a new or different protocol template.

At step 309, the system may determine, based on the search from step 306, whether there is a new CAP/other cancer protocol template. This may be performed by a web data extraction algorithm, which would extract data from an associated website. The new protocol information may then be parsed, searched, and reformatted. Algorithms may be applied to determine whether a new protocol or guideline has been determined. For example, the trained system may keep track of the current version of all protocols or guidelines and search for a new version of a guideline. At step

309, if a new template and/or protocol is not found, the trained system may report that no new template or protocol exists to a user. Further, the trained system may record that no new protocol or template has been found. If a new protocol and/or guideline is determined, the system may save and/or output the new protocol and/or guideline to an external user or a digital storage device 109.

At step 312, upon determining a new protocol and/or guideline exists, the trained system may parse the new protocol or guideline. The system may also parse data using structured approaches for data that is structured (e.g. XLS<XML, CSV) and use free-test Regular Expression and Natural Language Processing to extract fields in PDF files and word documents. The structured worksheets may be stored in one or more storage devices 109. The document that has the new protocol or guideline may be referred to as a template. The parsed information may be stored in one or more storage devices 109. The parsed information may be saved as a PDF, Word, comma-separated values ("CSV"), or any other word processing document.

If a new protocol or guideline is determined, then the trained system may proceed to step 382. In another example, step 382 may occur when an external user provides a new protocol, guideline, or determined template to the trained system (e.g., by the physician servers 121, hospital servers 122, clinical trial servers 123, research lab servers 124, and/or laboratory information systems 125, or by an external source). At step 382, the trained system may determine new synoptic report and/or worksheet based on the new guideline and/or protocol.

At step 315, the trained system may determine whether a new synoptic report and/or worksheet for the new guideline and/or protocol may be determined by an external user or automatically. For example, an external user may be able to select whether to provide a synoptic worksheet/report, or select whether to have the trained system create a synoptic worksheet/report. In one example, the trained system may automatically create the synoptic worksheet/report. In other examples, the trained system may wait to create a synoptic worksheet/report until a user requests this action.

At step 318, the trained system may determine a synoptic report/worksheet based on the parsed data from step 312. The trained system may automatically create a synoptic report/worksheet based on the parsed data (e.g., step 318). For a synoptic report/worksheet to be created automatically, the system may determine the file format of the parsed data such as PDF, word document, HTML, XML, XLS, CSV, etc.) and input the data into a centralized storage system. This information may be extracted from the file and moved to a Dataframe or database table for example (e.g., digital storage 109). The data may then be fully structured.

At step 321, upon determining that a worksheet/synoptic report will not be created automatically, a user may create and upload a worksheet/synoptic report to the trained system. In one example, a pathologist/researcher may be alerted that a new guideline has been created (e.g., at step 309) and then the individual may utilize the parsed data (e.g., from step 312) to manually create a synoptic report/worksheet based on the new guideline.

At step 324, the new worksheet/synoptic report may be saved in one or more storage devices 109.

At step 327, an external system may receive digital medical images of tissue analyzed according to the new protocol new worksheet/report from step 382. For example, upon determining a new protocol and a corresponding worksheet/report, a hospital and/or research center may then begin performing diagnosis of digital medical images (e.g., WSIs) using the new protocol worksheet/report determined during step 382. These new slides may be annotated/marked in data as being processed/analyzed under the new protocol.

At step 384, the trained system may begin training a machine learning system to analyze a digital medical image according to the newly determined protocol and/or guideline. Steps 384 may proceed when a particular number of slides analyzed under a new protocol or guidelines have been determined.

At step 330, the trained system may receive digital medical images of tissue analyzed according to the new protocol new worksheet/report from an external system (e.g., from step 327). The annotated images may be received by physician servers 121, hospital servers 122, clinical trial servers 123, research lab servers 124, and/or laboratory information systems 125, or by an external source. The trained system may then receive the analyzed digital medical images as input for training data from the one or more digital storage devices 109. The trained system or a user may define a threshold number of slides, N, needed to perform training or retraining of the machine learning algorithm. For a simple phenotype N may be a values in the hundreds, e.g., 500 slides. For a complex phenotype, N may be a value in the thousands such as 5000 slides. In another example, the trained system may receive training slides or other electronic images from an external source such as another hospital that has already incorporated the new protocol.

At step 333, the trained system may determine that an adequate number of training slides N has been received. The trained system may then begin training a machine learning system. When a new protocol and/or guideline has been determined, step 333 may be performed at specific time intervals such as once a day or once a week. In another example, step 333 may constantly monitor the number of slides N and move to step 336 immediately when the threshold number of slides N has been determined and/or exceeded.

At step 336, the system may split the data. The data may be split into sets that are non-overlapping on the patient level so the system may be trained with a first set of slides and evaluated with the other set of slides. The data may also be randomly split. In another example, the data may be set into three subsets: a subset to train, a subset to validate, and a subset to test.

At step 339, the system may fine-tune the model. For example, the model may be fine-tuned with an updated label definition, where one takes an existing checkpoint and then fine tunes it using the new updated label definition. The system may use a variety of models as a starting model for training. In one embodiment, the model may start as a model that was already trained on a previous version of the protocol. In another embodiment, the system may take a randomly initialized model to train. In another embodiment, the system may take a pre-trained model that is not trained on medical data to begin with and use this model as a starting point. In this embodiment, the pre-trained model may be trained on non-medical data such as natural images (e.g., Imagenet). Alternatively, the pre-trained model may be a publicly available pre-trained model that is trained on natural images (e.g. through transfer learning). The natural images may be objects such as airplanes, cars, cats, dog, flowers, fruits, motorbikes, etc.

After the system utilizes one of the starter models, the system may be trained and fine-tuned. Fine-tuning may refer to the process/technique of training and outputting a layer from scratch and having the other layers of the model be optimized (fine-tuned) with, for example, a small learning rate. The model may perform the training on two or more types of initial models and determine which model is most accurate. For example, a first model may be pre-trained initialized model and the second model may be a random initialized model that is compared using "Area Under the Curve" (AUC) of the "Receiver Operating Characteristics" (ROC).

Figure 4:
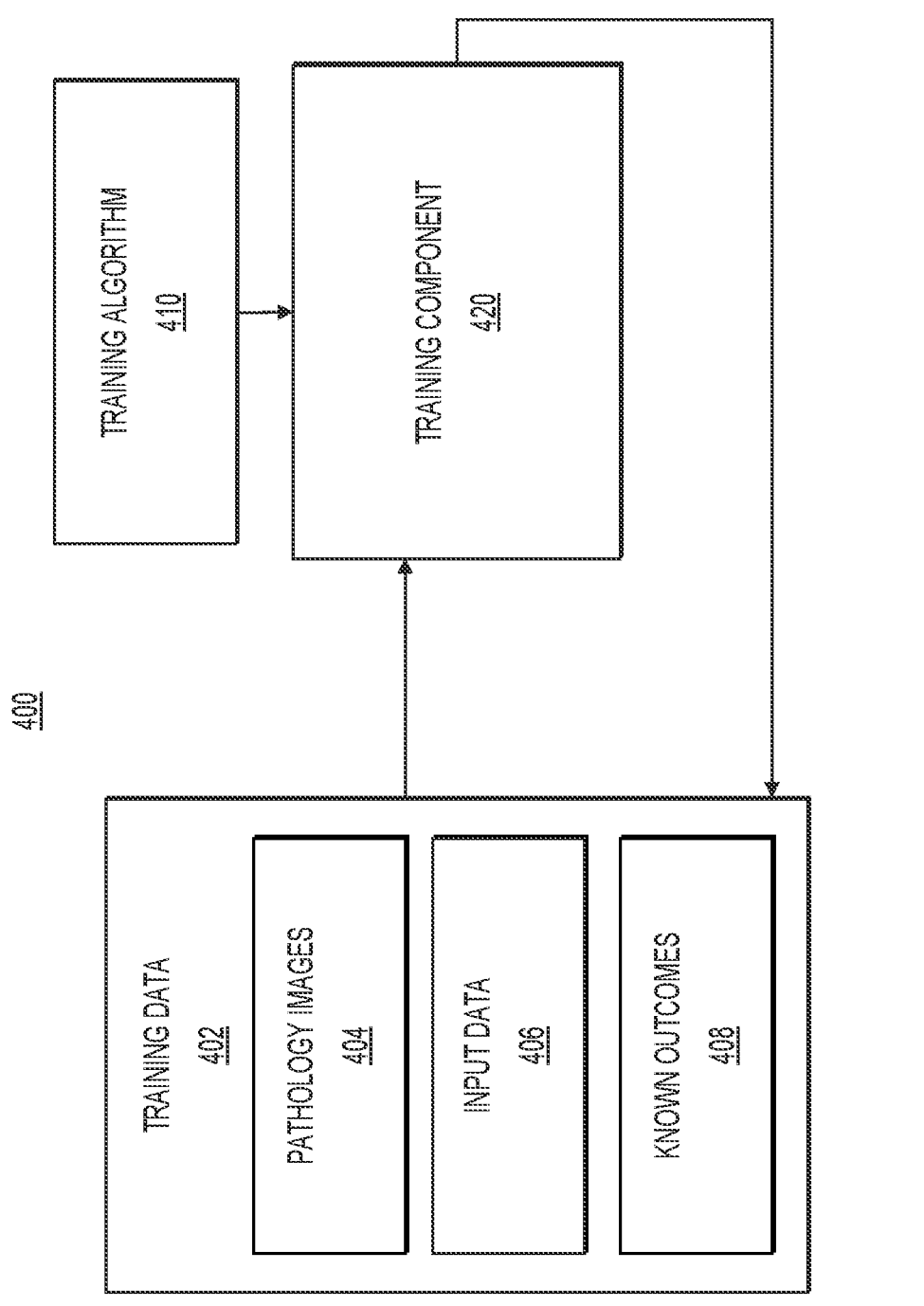
FIG. 4 illustrates an exemplary block diagram of a training module, according to an exemplary embodiment of the present disclosure.

An exemplary training of the machine learning module is displayed in FIG. 4. FIG. 4 shows an example training module 400 to train the trained machine learning system of step 384. As shown in FIG. 4, training data 402 may include one or more of pathology images 404 (e.g., digital representation of biopsied images), input data 406 (e.g., a digital pathology image dataset and corresponding annotations, diagnosis, or measurements), and known outcomes 408 (e.g., preferred outputs of machine learning systems) related to the input data 406. The training data 402 and a training algorithm 410 may be provided to a training component 420 that may apply the training data 402 to the training algorithm 410 in order to generate the machine learning system of step 382.

The training data 402 may be generated and/or provided by one or more of the systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc., and/or (b) digitized tissue samples from a 3D imaging device, such as microCT. Training data 402 may further come from the determined slides from step 330.

An exemplary embodiment of the machine learning system described herein may provide analysis of a digital medical image according to a new and/or selected protocol/guideline, based on a worksheet or report. The analysis may include a diagnosis and/or measurement.

At the end of step 339, the system may have determined a new machine learning model capable of analyzing a digital medical image according to a new protocol and/or guideline. This may be saved to digital storage 109.

At step 342, the fine-tuned model 339 may be evaluated. This evaluation may include running the determined machine learning system on the digital medical images from step 336 that were not used for training. The assessment may be performed by analyzing the fine-tuned models according to AUC, sensitivity, specificity, etc. Further, the system may determine heatmaps and other visual prediction to be evaluated and compared. In one example, the fine-tuned models may have AUC scores compared by an algorithm to receive an approved evaluation.

After the model is trained and fine-tuned, at step 345 the machine learning model may then be evaluated by pathologists/researchers. This may include inserting additional training images or additional digital medical images and having an external user review the outputs. At step 348, the trained system may receive an external input regarding whether the performance of the machine learning system is satisfactory.

At step 351, upon determining an external input that performance of the trained machine learning system is not satisfactory, the trained system may increase the value for N, corresponding to the number of slides needed for training and be sent to train more once more training slides are available. A user may be able to select a new threshold number of slides N. In another example, the system may automatically determine a new threshold number of slides N, such as requiring an additional 100 or 1000 slides. Once N slides are received, steps 330-348 may be partially or entirely repeated.

At step 348, upon determining an input that performance of the machine learning model is satisfactory, the trained machine learning module may be saved to one or more digital storage systems 109. The trained machine learning system may then be capable of being utilized by an external user (e.g., a pathologist from a hospital or research lab).

At steps 386, the trained system may determining that study requirements have been met for the machine learning system determined at steps 384. Steps 386 may be performed, for example, if the determined machine learning system performs beyond a predetermined metric, then the system may begin to prepare for a potential study by the FDA/CE to gain model approval. In another example, steps 386 may be performed if the trained system receives a machine learning system from an external system.

At step 354, the trained system may first determine a required study for a new machine learning system. For example, the trained system (e.g., protocol tool 141) may be capable of receiving study requirements. An external user may input a study type and study requirements to the trained system. For example, the user may manually enter the requirements into a configuration (e.g., a JavaScript Object Notation) file. In another example, the trained system may know from previous guidelines or an automated website scrape what the requirement configurations are. The system may analyze all data in a received DataFrame and analyze all of the covariates/cofounding factors and based on this select a study configuration that is statistically significantly powered. The study requirements could be for academia, Conformite Europeenne, a study for a pharmaceutical company, or a study for the Food and Drug Administration.

Based on the required study, at step 354 the trained system may determine the study requirements such as the minimum number of slides needed for testing. Additional requirements may include that the natural distributions of rare conditions is covered, proving that the model generalizes to all conditions even rare ones and that the system doesn't performance worse on certain rare conditions, or for grade groups (e.g., Gleason grading) in prostate there may be minimum requirements in number of grades 6, 7, 8, 9, and/or 10 digital medical images. Once the number of slides necessary for a study is determined, the system may then keep track of how many slides are analyzed according to the new protocol and using the determined machine learning system at a hospital/research center at step 357. This may be performed by receiving a notification (e.g., from the systems 110, physician servers 121, hospital servers 122, clinical trial servers 123, research lab servers 124, and/or laboratory information systems 125) each time the determined machine learning system from steps 384 _i_ utilized. Further, the output of the determined machine learning system may be provided to the trained system (e.g., the protocol tool 141).

At step 366, upon determining a minimum threshold is met for a study at step 360 and 363, the trained system may output a notification to a user or a hospital/research center, that they are able to request a regulatory group to conduct a study.

FIG. 5 is a flowchart illustrating an example method for determining an AI model to analyze digital medical images utilizing a new version of a guideline/protocol.

At step 502, a determination of whether a pathology protocol is accessible may be performed using an automated route.

At step 504, a first set of one or more training images may be determined, the first set of one or more training images comprising digital medical images annotated utilizing the pathology protocol.

At step 506, the training images may be provided to a machine learning model capable of analyzing digital medical images according to the pathology protocol or guideline.

At step 508, the step of providing training images to a machine learning may further include determining a starting model; splitting the first set of one or more training images into a training set A and an evaluation set B of digital medical images; fine tuning the starting model with the training set A to determine the machine learning model; evaluating the machine learning model with the training set B; and upon receiving a passing evaluation, saving the determined machine learning model to digital storage.

Figure 6:
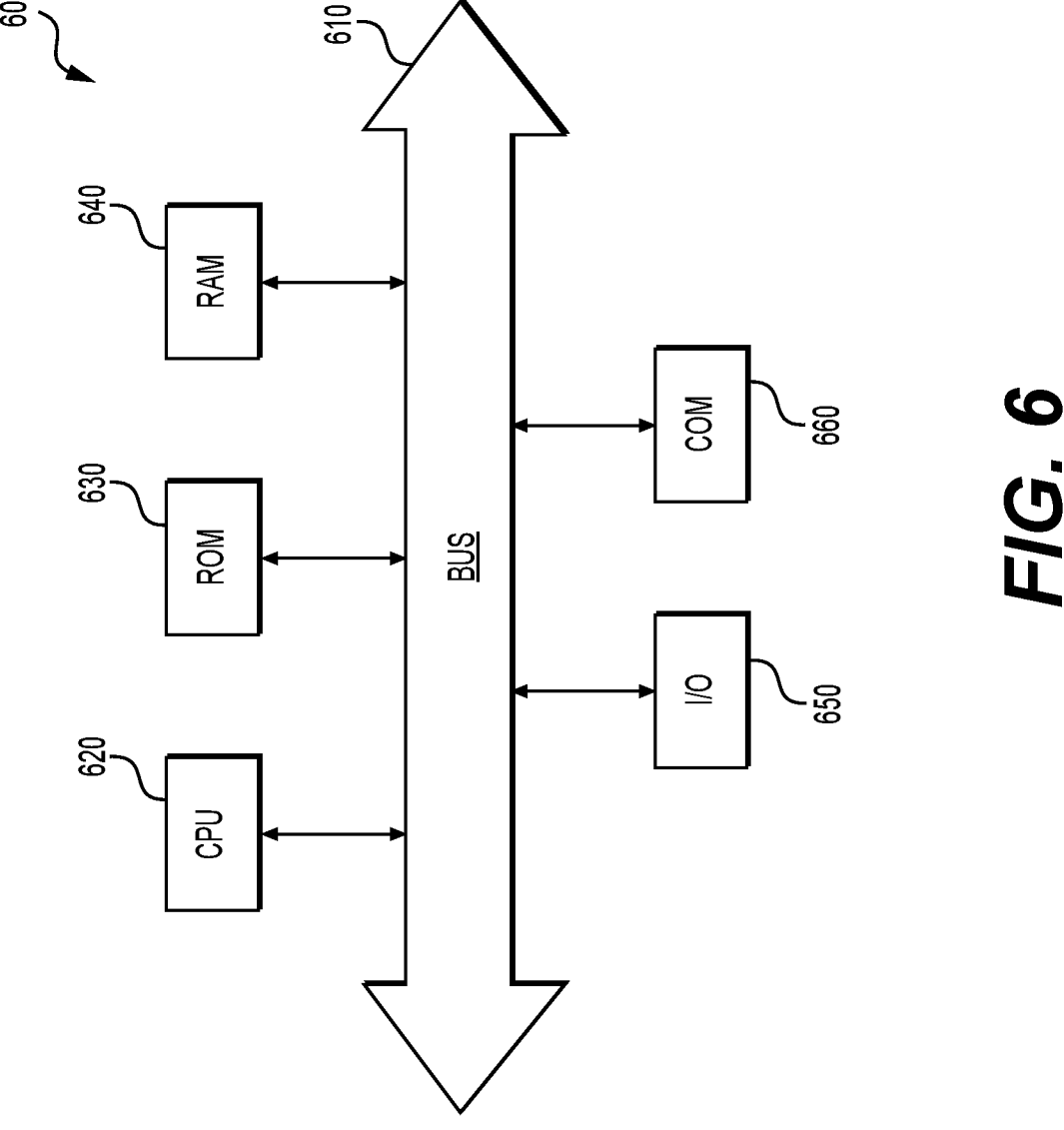
FIG. 6 depicts an example of a computing device that may execute techniques presented herein, according to one or more embodiments.

As shown in FIG. 6, device 600 may include a central processing unit (CPU) 620. CPU 620 may be any type of processor device including, for example, any type of special purpose or a general-purpose microprocessor device. As will be appreciated by persons skilled in the relevant art, CPU 620 also may be a single processor in a multi-core/multi-processor system, such system operating alone, or in a cluster of computing devices operating in a cluster or server farm. CPU 620 may be connected to a data communication infrastructure 610, for example a bus, message queue, network, or multi-core message-passing scheme.

Device 600 may also include a main memory 640, for example, random access memory (RAM), and also may include a secondary memory 630. Secondary memory 630, for example a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 630 may include similar means for allowing computer programs or other instructions to be loaded into device 600. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 600.

Device 600 also may include a communications interface ("COM") 660. Communications interface 660 allows software and data to be transferred between device 600 and external devices. Communications interface 660 may include a modem, a network interface (such as an Ethernet card), a communications port, a PCMCIA slot and card, or the like. Software and data transferred via communications interface 660 may be in the form of signals, which may be electronic, electromagnetic, optical or other signals capable of being received by communications interface 660. These signals may be provided to communications interface 660 via a communications path of device 600, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 600 may also include input and output ports 650 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments may be apparent to those skilled in the art from consideration of the specification and practice of the invention disclosed herein. It is intended that the specification and examples be considered as exemplary only.

What is claimed is:

1. A computer-implemented method for processing electronic medical images comprising:

determining, using an automated routine, whether a pathology protocol is accessible;

determining a first set of one or more training images, the first set of one or more training images comprising digital medical images annotated utilizing the pathology protocol; and providing the training images to a machine learning model capable of analyzing digital medical images according to the pathology protocol or guideline, the providing further including:

determining a starting model;

splitting the first set of one or more training images into a training set A and an evaluation set B of digital medical images;

fine tuning the starting model with the training set A to determine the machine learning model;

evaluating the machine learning model with the training set B; and upon receiving a passing evaluation, saving the determined machine learning model to digital storage.

2. The method of claim 1, wherein upon determining that a pathology protocol is accessible further comprises:

parsing data of the pathology protocol;

determining a new synoptic report based on the parsed data; and providing the new synoptic report to the machine learning model.

3. The method of claim 1, wherein the training images include annotations of digital medical images, the annotations being performed according to the pathology protocol, wherein the annotations comprise measurements, designations, and/or diagnosis.

4. The method of claim 1, wherein determining whether a pathology protocol is available is performed iteratively at predetermined time intervals.

5. The method of claim 1, wherein the pathology protocol is a new cancer protocol template.

6. The method of claim 1, wherein the pathology protocol is a PDF, word document, or CSV document.

7. The method of claim 1, wherein the starting model in a machine learning model trained on a previous version of the pathology protocol.

8. The method of claim 1, further including:

determining a new synoptic report based on the pathology guideline, the machine learning model being trained to fill out the new synoptic report when analyzing new digital medical images.

9. The method of claim 8, wherein determining a new synoptic report includes automatically creating, by a machine learning system and/or a rules-based artificial intelligence algorithm, a new synoptic report.

10. The method of claim 8, wherein determining a new synoptic reports includes receiving a synoptic report corresponding to the pathology protocol or guideline from an external user or system.

11. The method of claim 1, wherein the machine learning model is not determined until the determined first set of one or more training images exceed a threshold value of training images.

12. The method of claim 1, further including:

determining the machine learning model has been applied to a predetermined number of slides to meet a study requirement.

13. A system for processing electronic medical images, the system comprising:

at least one memory storing instructions; and at least one processor configured to execute the instructions to perform operations comprising:

determining, using an automated routine, whether a pathology protocol is accessible;

determining a first set of one or more training images, the first set of one or more training images comprising digital medical images annotated utilizing the pathology protocol; and providing the training images to a machine learning model capable of analyzing digital medical images according to the pathology protocol or guideline, the providing further including:

determining a starting model;

splitting the first set of one or more training images into a training set A and an evaluation set B of digital medical images;

fine tuning the starting model with the training set A to determine the machine learning model;

evaluating the machine learning model with the training set B; and upon receiving a passing evaluation, saving the determined machine learning model to digital storage.

14. The system of claim 13, wherein upon determining that a pathology protocol is available further comprises:

parsing data of the pathology protocol;

determining a new synoptic report based on the parsed data; and providing the new synoptic report to the machine learning model.

15. The system of claim 13, wherein the training images include annotations of digital medical images, the annotations being performed according to the pathology protocol, wherein the annotations comprise measurements, designations, and/or diagnosis.

16. The system of claim 13, wherein determining whether a pathology protocol is available is performed iteratively at predetermined time intervals.

17. The system of claim 13, wherein the pathology protocol is a new cancer protocol template.

18. The system of claim 13, wherein the pathology protocol is a PDF, word document, or CSV document.

19. The system of claim 13, wherein the starting model in a machine learning model trained on a previous version of the pathology protocol.

20. A non-transitory computer-readable medium storing instructions that, when executed by a processor, perform operations processing electronic medical images, the operations comprising:

determining, using an automated routine, whether a pathology protocol is accessible;

determining a first set of one or more training images, the first set of one or more training images comprising digital medical images annotated utilizing the pathology protocol; and providing the training images to a machine learning model capable of analyzing digital medical images according to the pathology protocol or guideline, the providing further including:

determining a starting model;

splitting the first set of one or more training images into a training set A and an evaluation set B of digital medical images;

fine tuning the starting model with the training set A to determine the machine learning model;

evaluating the machine learning model with the training set B; and upon receiving a passing evaluation, saving the determined machine learning model to digital storage.

* * * * *